United States Patent
Alghunaim et al.

(10) Patent No.: US 11,414,645 B2
(45) Date of Patent: Aug. 16, 2022

(54) THERMORESPONSIVE CELL CULTURE SUPPORTS

(71) Applicants: Abdullah Alghunaim, Riyadh (SA); Bi-min Zhang Newby, Hudson, OH (US)

(72) Inventors: Abdullah Alghunaim, Riyadh (SA); Bi-min Zhang Newby, Hudson, OH (US)

(73) Assignee: The University of Akron, Akron, OH (US)

( * ) Notice: Subject to any disclaimer, the term of this patent is extended or adjusted under 35 U.S.C. 154(b) by 862 days.

(21) Appl. No.: 16/239,671

(22) Filed: Jan. 4, 2019

(65) Prior Publication Data
US 2019/0136179 A1 May 9, 2019

Related U.S. Application Data

(62) Division of application No. 15/458,254, filed on Mar. 14, 2017, now abandoned.

(60) Provisional application No. 62/341,703, filed on May 26, 2016.

(51) Int. Cl.
| | | |
|---|---|---|
| *C12N 5/00* | (2006.01) |
| *C08F 120/54* | (2006.01) |
| *C08K 5/5435* | (2006.01) |
| *C08K 5/548* | (2006.01) |
| *C08K 5/5419* | (2006.01) |
| *C09D 133/24* | (2006.01) |

(52) U.S. Cl.
CPC .......... *C12N 5/0068* (2013.01); *C08F 120/54* (2013.01); *C08K 5/548* (2013.01); *C08K 5/5419* (2013.01); *C08K 5/5435* (2013.01); *C09D 133/24* (2013.01); *C12N 2533/30* (2013.01); *C12N 2537/00* (2013.01); *C12N 2539/10* (2013.01)

(58) Field of Classification Search
CPC ............ C12N 2539/10; C12N 2537/00; C12N 2533/30; C09D 133/24
See application file for complete search history.

(56) References Cited

U.S. PATENT DOCUMENTS

2014/0193911 A1* 7/2014 Newby ................ C12N 5/0662
435/396

OTHER PUBLICATIONS

Alghunaim et al. Retention of Poly(N-Isopropylacrylamide) on 3-Aminopropyltriethoxysilane; Biointerphases, vol. 12, No. 2, pp. 1-10. (Year: 2017).*
Renoud et al. Functionalization of Titanium with Chitosan via Silanation: Evaluation of Biological and Mechanical Performances; PLoS One, vol. 7, No. 7, pp. 1-10. (Year: 2012).*
Li et al. Submicronic Films of Surface-Attached Polymer Network With Temperature-Responsive Properties; Langmuir, vol. 31, pp. 11516-11524. (Year: 2015).*
Sui et al. Poly(N-Isopropylacrylamide)-Poly(Ferrocenylsilane) Dual-Responsive Hydrogels: Synthesis, Characterization and Antimicrobial Applications; Polymer Chemistry, vol. 4, pp. 337-342. (Year: 2013).*

* cited by examiner

*Primary Examiner* — Neil P Hammell
*Assistant Examiner* — Paul C Martin
(74) *Attorney, Agent, or Firm* — Renner Kenner Greive Bobak Taylor & Weber

(57) ABSTRACT

The present invention relates to a cell culture support comprising a substrate and a polymeric blend layer bound to the substrate. The polymeric blend layer comprises at least one thermoresponsive polymer and at least one coupling agent. The coupling agent is a non-protein coupling agent that has functional thiol, ester, epoxy, or aldehyde groups. The cell culture support further includes cells supported by the polymeric blend layer, wherein the thermoresponsive polymer provides for temperature induced detachment of the cells and/or cell sheets.

10 Claims, 3 Drawing Sheets

THERMORESPONSIVE CELL CULTURE SUPPORTS

RELATED APPLICATIONS

This application is divisional application of abandoned U.S. application Ser. No. 15/458,254 filed on Mar. 14, 2017, which claims the benefit of U.S. Provisional Application Ser. No. 62/341,703 filed May 26, 2016.

STATEMENT REGARDING FEDERALLY SPONSORED RESEARCH OR DEVELOPMENT

This invention was made with government support under NIH 1R15GM097626-01A1 awarded by National Institutes of Health. The government has certain rights in the invention.

TECHNICAL FIELD

The present invention relates to cell culture supports and methods of making cell culture supports. More particularly, this invention relates to thermoresponsive polymeric cell culture supports that are receptive to cell attachment and subsequent rapid cell sheet detachment. These supports are suitable for use, for example, in biomedical applications such as tissue engineering.

BACKGROUND OF THE INVENTION

Previous methods of preparing thermo-responsive cell culture supports have used two primary approaches, namely electron beam irradiation or plasma polymerization, to covalently graft poly (N-isopropylacrylamide) (pNIPAAm) chains onto tissue culture polystyrene dishes. The complicated procedures and apparatus required in these methods prevent a cost-effective adoption of this technology for specific applications. Furthermore, previous methods have generally required the use of added adhesive proteins from other individuals or other species to enhance cell attachment, and such foreign additions tend to cause immunogenic reactions of the cell sheet products after transplantation. Other methods that do not employ thermo-responsive polymers (TRPs) for detachment and harvesting of cell sheets from cell culture supports have employed proteolytic enzymes (e.g. trypsin) or mechanical agitations, which have resulted in damage to cells and their excreted extracellular matrix (ECM), thus negatively affecting their biological functions.

Nagase et al., as disclosed in J. R. Soc. Interface (2009) 6, S293-S309 and incorporated herein by reference, teach thermoresponsive micropatterned surfaces using electron beam polymerization techniques to allow the selective adhesion and growth of, for example, rat primary hepatocytes and bovine carotid endothelial cells. U.S. Pub. No. 2010/0216242 discloses a cell culture support including a polymer layer exhibiting thermoresponsiveness and a cell culture region obtained by plasma-treating a surface layer portion thereof with a reactive gas while limiting additions of cell adhesion proteins, such as collagen. However, these methods are still too expensive for wide-spread use.

Fujita et al., as disclosed in Biotechnology and Bioengineering, Vol. 103, No. 2, Jun. 1, 2009 and incorporated herein by reference, teach fabricating a cell sheet-polymer film complex involving a temperature-sensitive polymer in which cells are attached to a temperature-sensitive poly-N-isopropylacrylamide film mixed with laminin and collagen IV. As previously mentioned, added adhesive proteins are undesirable as they may deleteriously cause immunogenic reactions.

An approach reported by Nash et al., as disclosed in the Journal of Materials Chemistry, Vol. 22, May 10, 2012, utilized spin coating to deposit temperature-sensitive poly-N-isopropylacrylamide without the use of adhesive proteins. The resulting temperature-sensitive substrate allows for the attachment and detachment of cell sheets. However, the dissolution of poly-N-isopropylacrylamide into the cell culture medium upon cooling is undesirable.

There is a need in the art for cell culture supports and methods of growing and releasing cell sheets therefrom that do not suffer from these various drawbacks. Also, the method should be simple and cost-effective to make it economically feasible for general biomedical applications.

SUMMARY OF THE INVENTION

The present invention provides a simple and cost effective approach to create thermoresponsive cell culture supports using commercially available materials. This is beneficially achieved without using expensive electron beam irradiation or plasma polymerization techniques. In addition, the present method is advantageously devoid of additional adhesive proteins and is further devoid of mechanical agitation or enzymatic aided detachment methods. The cell culture supports of the present invention employ a polymeric blend comprising a thermoresponsive polymer and a coupling agent that can enhance cell attachment and growth of cells on the cell culture support. The cell culture supports of this invention support cell attachment and proliferation as well as rapid cell sheet detachment.

In a first embodiment, the present invention provides a cell culture substrate comprising: a substrate; a polymeric blend layer bound to said substrate, wherein the polymeric blend layer comprises at least one thermoresponsive polymer and at least one coupling agent, and wherein the coupling agent is a non-protein coupling agent and has functional thiol, ester, epoxy, or aldehyde groups; and cells supported by said polymeric blend layer, wherein said thermoresponsive polymer provides for temperature induced detachment of said cells.

In a second embodiment, the present invention provides a cell culture support as in the first embodiment, wherein the substrate is selected from the group consisting of polymeric materials, glasses, ceramics, metals, metal oxides, hydrated metal oxides, and combinations thereof.

In a third embodiment, the present invention provides a cell culture support as in either the first or second embodiment, wherein the at least one thermoresponsive polymer is selected from the group consisting of poly (N-isopropylacrylamide) (PNIPAAm), poly(N,N-diethylacrylamide) (PDEAAm), poly(N-vinlycaprolactam) (PVCL), poly[2-(dimethylamino)ethyl methacrylate] (PDMAEMA), and poly (ethylene oxide) (PEO), 2-oxazoline (Pox), such as poly(2-ethyl-2-oxazoline), poly(2-cyclopropyl-2-oxazoline), poly (2-n-propyl-2-oxazoline), poly(2-isopropyl-2-oxazoline); or the group consisting of poly(2-oxazine) (POZIs), such as poly(2-ethyl-oxazine), poly(2-n-propyl-oxazine), and combinations thereof.

In a fourth embodiment, the present invention provides a cell culture support as in any of the first through third embodiments, wherein the at least one thermoresponsive polymer is poly (N-isopropylacrylamide) represented by the formula:

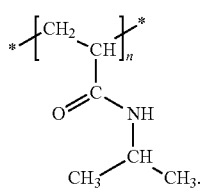

In a fifth embodiment, the present invention provides a cell culture support as in any of the first through fourth embodiments, wherein the at least one network forming adhesion promoter is an aminosilane.

In a sixth embodiment, the present invention provides a cell culture support as in any of the first through fifth embodiments, wherein the at least one coupling agent is selected from the group consisting of 3-Acetoxypropyltrimethoxysilane (AOPTMS), 3-Mercaptopropyltrimethoxysilane (MPTMS), Triethoxysilylbutyraldehyde (TESBA), 2-(3,4-epoxycyclohexyl)ethyltrimethoxysilane (ECHETMS), 3-(2,3-epoxypropoxy)propyltrimethoxysilane (EPPTMS), and combinations thereof.

In a seventh embodiment, the present invention provides a cell culture support as in any of the first through sixth embodiments, wherein the at least one coupling agent is Triethoxysilylbutyraldehyde (TESBA), represented by the formula:

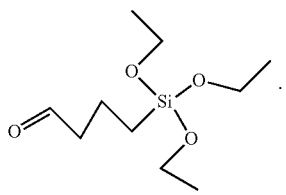

In an eighth embodiment, the present invention provides a cell culture support as in any of the first through seventh embodiments, wherein the at least one coupling agent is 3-Mercaptopropyltrimethoxysilane (MPTMS), represented by the formula:

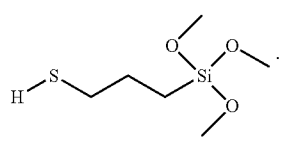

In a ninth embodiment, the present invention provides a cell culture support as in any of the first through eighth embodiments, wherein the polymer blend is characterized as having a thermoresponsive polymer to coupling agent ratio (TRP:CA) of from about 99:1 to about 10:90, and wherein the polymer blend layer is cured to produce a film.

In a tenth embodiment, the present invention provides a cell culture support as in any of the first through ninth embodiments, wherein the polymeric blend layer is devoid of adhesive proteins, plasma treatment, and e-beam treatment.

In an eleventh embodiment, the present invention provides a cell culture support as in any of the first through tenth embodiments, wherein the support supports said cells such that said temperature induced detachment is achieved without mechanical agitation or enzymatic aided detachment methods.

In a twelfth embodiment, the present invention provides a method of making a cell culture complex comprising: providing a substrate; blending at least one thermoresponsive polymer and at least one coupling agent having functional thiol, ester, epoxy, or aldehyde groups to provide a polymeric blend; applying a thin film of said polymeric blend to the substrate to provide a polymeric blend layer on the substrate; curing the polymeric blend layer on the substrate to provide a cell culture support; and depositing cells onto said cell culture support, wherein the cells may optionally further comprise medium, to provide a cell culture complex.

In a thirteenth embodiment, the present invention provides a method of making a cell culture complex as in the twelfth embodiment, wherein the cultured cell layer comprises cells further characterized as anchor dependent cells.

In a fourteenth embodiment, the present invention provides a method of making a cell culture complex as in either the twelfth or thirteenth embodiment, wherein the cultured cell layer comprises cells further characterized as adhesive cells.

In a fifteenth embodiment, the present invention provides a method of making a cell culture complex as in any of the twelfth through fourteenth embodiments, wherein the cultured cell layer comprises cells selected from the group consisting of fibroblasts, myoblasts, myotube cells, corneal cells, vascular endothelial cells, smooth muscle cells, cardiomyocytes, dermal cells, epidermal cells, mucosal epithelial cells, mesenchymal stem cells, ES cells, iPS cells, osteoblasts, osteocytes, chondrocytes, fat cells, neurons, hair root cells, dental pulp stem cells, β-cells, hepatocytes, and combinations thereof.

In a sixteenth embodiment, the present invention provides a method of making a cell culture complex as in any of the twelfth through fifteenth embodiments, wherein the cultured cell layer comprises cells and medium.

In a seventeenth embodiment, the present invention provides a method of making a cell culture complex as in any of the twelfth through sixteenth embodiments, wherein the thin film of said polymeric blend is spin-coated onto the substrate.

In an eighteenth embodiment, the present invention provides a method of making a cell culture complex as in any of the twelfth through seventeenth embodiments, wherein the polymeric blend layer is devoid of adhesive proteins, plasma treatment, and e-beam treatment; and wherein the detachment of the cultured cell layer is devoid of proteolytic enzymes or mechanical agitations.

In a nineteenth embodiment, the present invention provides a method of making a cell culture complex as in any of the twelfth through eighteenth embodiments, wherein the step of blending further includes creating a first solution of the at least one coupling agent in ethanol, creating a second solution of the at least one thermoresponsive polymer in ethanol, and combining the first solution with the second solution to provide the polymeric blend.

In a twentieth embodiment, the present invention provides a method of making a cell culture complex as in any of the twelfth through nineteenth embodiments, wherein the step of blending further includes creating a mixture of the at least one coupling agent and the at least one thermoresponsive polymer and dissolving the mixture in ethanol to provide the polymeric blend.

DETAILED DESCRIPTION OF ILLUSTRATIVE EMBODIMENTS

Embodiments of the present invention are based upon the discovery of a cell culture support comprising a polymeric blend layer including a thermoresponsive polymer (TRP) and coupling agent whose molecules can enhance attachment and growth of cells on a cell culture support. The polymeric blend layer is provided on an appropriate substrate, and the substrate and polymeric blend may be provided as a specific product for use in growing and harvesting cells. Advantageously, the cell culture support of certain embodiments provides for enhanced cell attachment (to create what is called herein a "cell sheet") and rapid subsequent cell sheet detachment, even though the cell culture supports are substantially devoid of proteins and enzymes previously employed to facilitate cell growth and harvest, respectively. Practice of the present invention has been found to be particularly useful in biomedical applications, such as tissue engineering, but it is also contemplated that the practice of this invention can be expanded to other applications in which cell culture supports are desired, such as in cell-based pharmaceutical studies and clinical therapeutics.

Figure 1A:
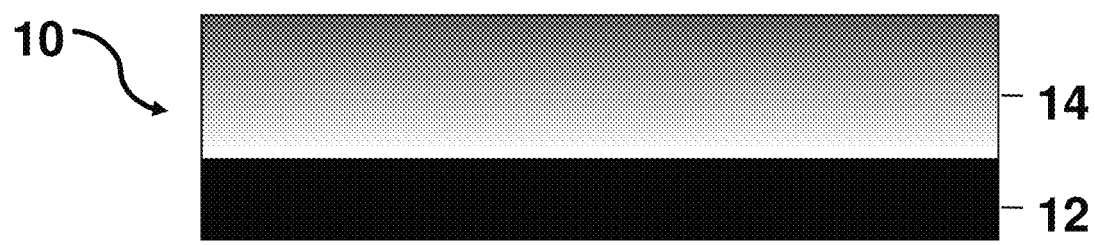
FIG. 1a illustrates an example of a cell culture support.

With reference to FIG. 1a, a cell culture support in accordance with this invention is shown and designated by the numeral 10. The cell culture support 10 includes a substrate 12 and a polymeric blend layer 14. The polymeric blend layer 14 is bounded to the substrate chemically through a coupling agent portion thereof by forming appropriate covalent bonds. The coupling agent is characterized as having functional thiol, ester, epoxy, or aldehyde groups. For example, when organosilanes, such as triethoxysilylbutyraldehyde (TESBA), are employed as the coupling agent, the organosilanes are bonded to a substrate containing hydroxyl groups by forming siloxane bonds. Since TESBA molecules also form a network by annealing, the polymer chains of the thermoresponsive polymer can be locked into the network, leading to the retention of the thermoresponsive polymer as well as the covalently bound coupling agent on the substrate.

Substrate

The substrate 12 can be provided in any useful form including, but not limited to, thin films, sheets, membranes, filters, nonwoven or woven fibers, hollow or solid beads, bottles, plates, tubes, rods, pipes, or wafers. The substrates can be porous or non-porous, rigid or flexible, transparent or opaque, clear or colored, and reflective or non-reflective. Suitable substrate materials are selected from the group consisting of polymeric materials, glasses, ceramics, metals, metal oxides, hydrated metal oxides, and combinations thereof.

Suitable polymeric materials include, for example, polysiloxanes, polycarbonates, celluloses, polyacrylates, polymethacrylates, polyamides, and polysulfones.

In one or more embodiments, polycarbonate, polydimethylsiloxane, and nylon 6,6 are useful in the practice of the present invention.

Suitable glass and ceramic substrate materials include, for example, sodium, silicon, aluminum, lead, boron, phosphorous, zirconium, magnesium, calcium, arsenic; gallium, titanium, copper, and combinations thereof. Glasses typically include various types of silicate-containing materials.

In one or more embodiments, commercially available glass slides (Fisher Scientific, Waltham, Mass., USA) or P(100) test type silicon-wafers (Silicon Quest International, Santa Clara, Calif.) are useful in the practice of the present invention. Silicon wafers may also be referred to herein as Si-wafers.

In one or more embodiments of the present invention, the substrate may be tailored to any size and shape suitable in accordance with the requirements of the specific application. For example, the substrate dimensions may be tailored to the desired resultant cell sheet size. Typically, for the purposes of illustrating examples herein, a polycarbonate sheet was cut into squares with a surface area of about 1 cm$^2$; however, the size of substrate contemplated may be virtually any size, and typically will range from about 0.01 to 100 cm$^2$.

The substrate is modified, if necessary, to provide functional groups at its surface suitable for covalently binding to the coupling agent and/or thermoresponsive polymer of the polymeric blend layer 14. In the practice of a particular embodiment of the present invention, the substrate used contains hydroxyl groups (—OH) to allow the covalent bonding of TESBA molecules to the substrate. Substrates containing amide (—NHC=O), carbonyl (—C=O), thiol (—SH) and sulfonyl (O=S=O) groups are also feasible.

Thermo-Responsive Polymer

Referring again to FIG. 1a, the cell culture support 10 of the present invention is comprised of a substrate 12 and a polymeric blend layer 14. The polymeric blend layer 14 includes at least one thermoresponsive polymer (TRP) and at least one coupling agent. The TRP is desired because cell sheets formed on TRPs may be harvested (i.e., detached readily from the cell culture support) by a simple change of temperature, the temperature causing a spontaneous detachment of the cell sheet due to the change of the polymer chains from a hydrophobic to a hydrophilic nature. TRPs have the ability to respond to a change in temperature and can be classified into two main types: TRPs possessing a lower critical solution temperature (LCST) and TRPs possessing an upper critical solution temperature (UCST).

As will be described more particularly herein, the response of the TRP to temperature changes is advantageously employed to safely harvest cells sheets grown on the polymeric blend layer of the cell culture support 10. In the hydrophobic state of the TRPs, the cell supports generally become more favorable for cells to attach and grow. As compared to the use of proteolytic enzymes (e.g. trypsin) or mechanical agitations to harvest cell sheets, using TRPs to harvest confluent cell sheets minimizes damage to cells and their excreted extracellular matrix (ECM), thus preserving their biological functions. Tissue engineering constructs based on cell sheets harvested according to the present invention allow increased cell-cell interactions and eliminate the risk of immunogenic materials present in scaffolds, wherein the scaffolds are the natural or synthetic biomaterials used in tissue engineering products to mimic ECM as a 3D cell culture environment. Furthermore, cell sheets harvested from TRPs can be patterned and assembled together to mimic the microarchitecture of native tissue, which is crucial for functional tissue regeneration.

The TRP is not particularly limited herein, and a variety of publicly known polymers or copolymers can be used as the thermoresponsive polymer. These polymers can be crosslinked as needed, but only to an extent that their thermoresponsive properties are not lost. In one or more embodiments, the TRP is chosen to have a molecular chain length greater than its entanglement length.

In some embodiments, the TRP can be selected from virtually any TRP that becomes hydrophobic and undergoes chain collapsing at an elevated temperature that is generally above room temperature and preferably near the incubation temperature useful for growing the desired cells, and subsequently becomes hydrophilic and undergoes chain expansion at a decreased temperature that is generally lower than the elevated temperature. In one or more embodiments, the elevated temperature is preferably above room temperature. In one or more embodiments, the decreased temperature is preferably near or below room temperature. Room temperature, or ambient temperature, is typically considered to be in the range from about 18° C. to about 25° C., more typically 20° C. to 23° C. In one or more embodiments, the decreased temperature is about room temperature.

In one or more embodiments, thermoresponsive polymers include various polyacrylamides, polyacrylamide derivatives and copolymers thereof.

In one or more embodiments, thermoresponsive polymers of the present invention are selected from the group consisting of poly-N-isopropylacrylamide (LCST=32° C.), poly-N—N-propylacrylamide (LCST=21° C.), poly-N—N-propylmethacrylamide (LCST=32° C.), poly-N-ethoxyethylacrylamide (LCST=~35° C.), poly-N-tetrahydrofurfurylacrylamide (LCST=~28° C.), poly-N-tetrahydrofurfurylmethacrylamide (LCST=~35° C.), poly-N,N-diethylacrylamide (LCST=32° C.), poly (C-isopropylacrylamide) (LCST=~32° C.) and combinations thereof (critical temperatures provided in parentheses).

In one or more other embodiments, the thermoresponsive polymers of the present invention are selected from the group consisting of poly-N-ethylacrylamide; poly-N-isopropylmethacrylamide; poly-N-cyclopropylacrylamide; poly-N-cyclopropylmethacrylamide; poly-N-acryloyl pyrrolidine; poly-N-acryloyl piperidine; polymethyl vinyl ether; alkyl-substituted cellulose derivatives such as methylcellulose, ethylcellulose, and hydroxypropylcellulose; polyalkylene oxide block copolymers typified by a block copolymer of polypropylene oxide and polyethylene oxide; and mixtures thereof.

In one or more embodiments, the thermoresponsive polymers of the present invention are selected from the group consisting of derivatives of 2-oxazoline (Pox), such as poly(2-ethyl-2-oxazoline) (LCST=~60° C.), poly(2-cyclopropyl-2-oxazoline) (LCST=~30° C.), poly(2-n-propyl-2-oxazoline) (LCST=~25° C.), poly(2-isopropyl-2-oxazoline) (LCST=~36° C.); or the group consisting of poly(2-oxazine) (POZIs), such as poly(2-ethyl-oxazine) (LCST=~56° C.), poly(2-n-propyl-oxazine) (LCST=~11° C.); and mixtures thereof.

In one or more embodiments of the present invention, suitable polymers with thermoresponsive properties are selected from the group consisting of poly (N-isopropylacrylamide) (pNIPAAm), poly(N,N-diethylacrylamide) (PDEAAm), poly(N-vinlycaprolactam) (PVCL), poly[2-(dimethylamino)ethyl methacrylate] (PDMAEMA), poly(ethylene oxide) (PEO), and combinations thereof.

Poly (N-isopropylacrylamide), a commonly available TRP that presents an attractive lower critical solution temperature (LCST), may also be referred to interchangeably herein as poly-N-isopropylacrylamide, poly(N-isopropylacrylamide), PNIPAAm, pNIPA, pNIPAA, pNIPAm, or pNIPAAm.

PNIPAAm may be represented by the formula:

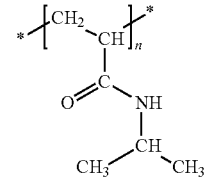

having both hydrophobic and hydrophilic groups, wherein the pNIPAAm chains collapse (lose H-bonds with $H_2O$ of the hydrophilic group) or extend (forms H-bonds with $H_2O$ of the hydrophilic group) depending on the temperature.

In one or more embodiments of the present invention, pNIPAAm (Sigma Aldrich, St. Louis, Mo., USA) is used as the thermoresponsive polymer. pNIPAAm is of special interest in bioengineering applications because of the phase change that it undergoes in a physiologically relevant temperature range. It has a lower critical solution temperature (LCST) of 32° C. in water. The polymer chains reside in a collapsed hydrophobic state above the LCST and in an extended hydrophilic state below LCST.

Coupling Agent

The polymeric blend layer 14 also includes a coupling agent. An effective coupling agent should exhibit a suitable solubility with the TRP to form an inter-diffused interphase and whose molecules can form a cross-linked network to lock in the TRP chains. The network formation should be achieved using a simple approach, e.g. thermal annealing at a temperature that causes no property changes to the thermoresponsive properties and the LCSTs of the TRPs. Furthermore, no thermal degradation of the TRPs occurred at the annealing temperature. By inter-locking TRP chains into the network, the chemical grafting of the TRP chains using facility intensive approaches, e.g. electron beam or plasma, is eliminated. In addition, the adhesion promoting properties of the coupling agents might provide the added advantages of enhancing cell attachment and growth, circumventing the contamination issues of using adhesion proteins. The coupling agents of the present invention are non-protein adhesion promoters. The coupling agents of the polymeric blend work to keep the TRP on the substrate surface.

In one or more embodiments, the coupling agents of the present invention bind or attach to the substrate. Without being bound by theory, attachment of the coupling agent to the substrate is accomplished through covalent bonds, H-bonding, or other attachment/binding means as are known in the art could also be present. The coupling agent also acts to entangle or interlock the TRP chains, thus immobilizing them to the substrate. Because most of the coupling agents selected have short backbone alkyl chains, they form a disordered and loose three-dimensional multilayer network, which is able to more easily entrap the TRP.

The coupling agent is characterized as having functional thiol, ester, epoxy, or aldehyde groups.

In one or more embodiments, suitable network forming coupling agents are selected from the group consisting of 3-Acetoxypropyltrimethoxysilane (AOPTMS), 3-Mercaptopropyltrimethoxysilane (MPTMS), Triethoxysilylbutyraldehyde (TESBA), 2-(3,4-epoxycyclohexyl)ethyltrimethoxysilane (ECHETMS), 3-(2,3-epoxypropoxy)propyltrimethoxysilane (EPPTMS), and combinations thereof. The coupling agents used in the present invention generally include at least two head groups and either a thiol, ester, epoxy or aldehyde end group.

In one or more embodiments, the coupling agent is triethoxysilylbutyraldehyde (TESBA) (from Gelest, Inc, Morrisville, Pa.). TESBA may be represented by the formula:

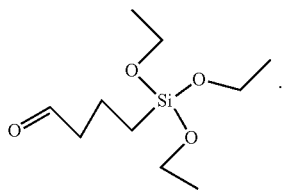

In one or more embodiments, the coupling agent is 3-Mercaptopropyltrimethoxysilane (MPTMS) (from Gelest, Inc, Morrisville, Pa.). MPTMS may be represented by the formula:

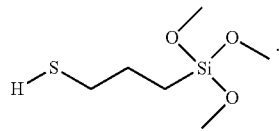

In one or more embodiments, the present invention is advantageously devoid of protein adhesion promoters, which are generally more complicated macromolecules and will not form the needed network to entrap TRP chains. Proteins as taught in the prior art are applied on top of the TRP layer, and are mainly adsorbed physically to the layer, thus they will most likely detach from the TRP layer and be retained with cells/cell sheets during harvesting. As such, these protein adhesives will be un-wanted foreign materials that cause contamination issues in the resulting cell sheets. In distinction, the network forming coupling agents used in the present invention will form a network and will be chemically anchored to the underneath substrate. Examples of unwanted proteins, of which the present invention is advantageously devoid of, include collagen, elastin, proteoglycans, glucosaminoglycans (hyaluronic acid, chondroitin sulfate, dermatan sulfate, heparan sulfate, heparin, keratin sulfate, etc.), fibronectin, laminin, hydronectin, gelatin, etc. in addition to RGD peptide, RGDS peptide, GRGD peptide, and GRGDS peptide.

Ingredient Ratios

In one or more embodiments of the present invention, the mass ratio of thermoresponsive polymer (TRP) to coupling agent in the polymeric blend layer 14 is from about 99:1 to about 10:90, in other embodiments from about 95:5 to about 75:25, in other embodiments from about 95:5 to about 85:15, in yet other embodiments from about 88:12 to about 92:8, and in still other embodiments from about 89:11 to about 91:9. In a particular embodiment, the mass ratio of thermoresponsive polymer to coupling agent is 90:10. In one or more embodiments, the mass percentage of TRP in the polymer blend comprising TRP and coupling agent, wherein the total of TRP and coupling agent forms 100 mass percent (mass %), is at least 75 mass %, in other embodiments at least 80%, in other embodiment at least 85%, in other embodiment at least 86%, in other embodiment at least 87%, in other embodiment at least 88%, in other embodiment at least 89%, and in yet other embodiments at least 90%. In one or more embodiments, the percentage of TRP in the polymeric blend layer 14, wherein the total of TRP and coupling agent is 100%, is at most 99 mass %, in other embodiments at most 98%, in other embodiment at most 95%, in other embodiment at most 94%, in other embodiment at most 93%, in other embodiment at most 92%, in other embodiment at most 91%, and in yet other embodiments at most 90%.

In particular embodiments employing pNIPAAm as the TRP and employing TESBA as the coupling agent, the above ratios are followed. In a particular embodiment, the polymeric blend layer 14 is a mixture of pNIPPAAm and TESBA at a mass ratio of pNIPPAAm:TESBA of from 10:90 to 90:10.

Substrate Preparation

For silica based substrates (e.g. glass, Si-wafer), the substrates will be first appropriately cleaned. This may be achieved by application of a freshly prepared piranha solution (i.e. 70/30 v/v concentrated sulfuric acid/30% technical grade hydrogen peroxide) for 30-60 minutes, followed by a thorough rinsing with deionized water, and then oxidation using either UV/ozone or plasma (oxygen or air) for 5-10 minutes to generate the needed —OH groups on the surface. Other cleaning methods that will remove the organic contamination are also feasible. Metal substrates will be sonicated, in sequence, using water-immiscible organic solvent (i.e. toluene, hexane), followed with water-miscible organic solvents (e.g. acetone, ethanol) and finally water, for 5-10 minutes each, to remove contaminants. Then they will also be oxidized using either UV/ozone or plasma (oxygen or air) for 5-10 minutes to generate, for example, —OH groups. For polymer substrates, they will be thoroughly rinsed with an appropriate solvent (e.g., ethanol), and then oxidized using either UV/Ozone or oxygen plasma for 5 minutes. Other linkages besides —OH groups to provide polymer blend bonding onto the substrate are also contemplated, including but not limited to ester linkages for example. In one or more embodiments, the polymer substrates will be rinsed and sonicated with appropriate solvents and then coated with a thin layer of silica based materials via the sol-gel process to provide a silica surface that can be modified to provide —OH groups. In these embodiments, siloxane bonding is promoted whereby the head groups are hydrolyzed and converted to —OH groups providing stable linkages onto the substrate.

Process of Preparing Cell Culture Substrates

In one or more embodiments, the polymeric blend layer is applied to the substrate by first forming the polymeric blend of the TRP and the coupling agent in a solution and then spin-coating, dip-coating or spreading the blend. The concentration of the solution can be tailored to achieve different film thickness. In one or more embodiments, the blended solution may comprise from about 0.5 to about 10 mass % total solute; in other embodiments from about 1 to about 5 mass % total solute; and in another embodiment from about 2 to 5 mass % total solute. In yet another embodiment, the concentration of the solute is about 3 mass %. In one or more embodiments, the polymeric blend is spin-coated to form a polymeric blend layer 14 on the substrate 12. Other techniques, as known in the art, may be used in addition to spin-coating including dip-coating and doctor blading.

The thickness of the polymeric blend layer may be variable and is not a critical parameter to the success of the cell culture support. Areas of excess thickness are not deleterious and will simply be washed away during preparation. In one or more embodiments, the thickness of the polymer layer is from about 10 nm to about 500 nm, in other embodiments from about 30 nm to about 400 nm, and in yet other embodiments from about 100 nm to about 200 nm. Generally, the thickness of the polymeric layer is greater than the thinnest layer (e.g. 8-10 nm) that can be created by spin-coating of the interested polymer solution. In one or more embodiments, the thickness of the polymeric blend layer is at least 15 nm, in other embodiments at least 18 nm, in yet other embodiments at least 25 nm, and in still other embodiments at least 30 nm.

Preparing of Cell Culture Support

In one or more embodiments, after applying the polymeric blend of FIG. 1a to the substrate 12 and thereby forming the polymeric blend layer 14, the polymeric blend layer 14 is thermally annealed to allow the formation of the network and anchoring of the polymeric blend layer 14 to the substrate. While thermal annealing is the easiest approach to achieve the desired bonding/network formation, other methods, such as UV irradiation, could be applied. Annealing serves to bond the coupling agent to the substrate and to form the network to lock the chains of the thermoresponsive polymer inside the network, intimately holding the polymeric blend layer 14 to the substrate 12. A suitable annealing temperature and time will be readily selected by those of skill in the art for a given polymeric blend layer 14 and substrate 12. The conditions (temperature, time) for annealing may vary depending upon the specific polymer blend type and ratio, but typically may range from about 80° C. to about 210° C. or higher for a time of about 24 hours to about 72 hours. In one or more embodiments, the polymer blend is annealed at a temperature from about 145° C. to about 205° C. for a time of about 24 hours to about 72 hours. In another embodiment, the polymer blend layer is annealed at about 160° C. for about 48 hours.

In a particular embodiment employing pNIPAAm and TESBA, the TESBA is cured by the application of heat, causing siloxane bonds to be formed. The pNIPAAm chains are interlocked in the TESBA network as the network is being formed.

After the step of annealing the polymeric blend layer 14, the substrate 12 and annealed polymeric blend layer 14 is placed inside a cell incubation dish, and the temperature is brought above the LCST of the thermoresponsive polymer. This will make the layer more hydrophobic, which is favorable for the attachment of cells and subsequently growth of a cell sheet. The layer can be reversed to its hydrophilic state, which is unfavorable for cells, by lowering the temperature, to allow for the detachment of the cell sheet. Due to the quick uptake of water for the retained TRP bulk layer, as compared to the brushes used by others, and the greater hydration of the layer, a quick cell sheet detachment would result. This will be disclosed in more detail herein below.

Figure 1B:
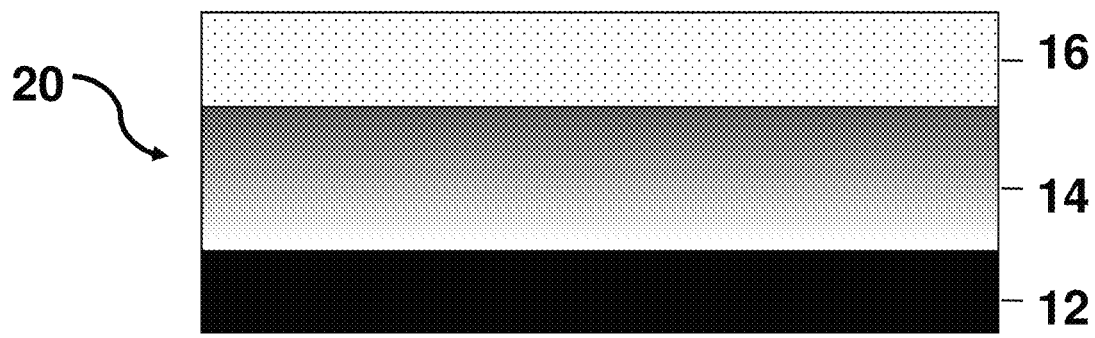
FIG. 1b illustrates an example of a cell culture complex.

The cell culture support 10 of the present invention, as shown in FIG. 1a, is useful for culturing anchor dependent cells. In one or more embodiments, the cultured cells are grown into cell sheets to provide, as schematically shown in FIG. 1b, a cell culture complex 20 with a cultured cell sheet 16 that can be subsequently harvested from the cell culture support by temperature induced (i.e. lowering the temperature) detachment. The cell culture complex 20 additionally includes a substrate 12 and a polymeric blend layer 14. The polymeric blend layer 14 is bounded to the substrate chemically through a coupling agent portion thereof by forming appropriate covalent bonds. The coupling agent is characterized as having functional thiol, ester, epoxy, or aldehyde groups. The detachment advantageously occurs rapidly. An advantage of the present invention is that the cell culture support 10 may be patterned and assembled together to mimic the microarchitecture of native tissue, which is crucial for functional tissue regeneration. Therefore, the cultured cell layer 16 may take on any size and shape desired for various applications. The cells to be cultured in the cell culture complex 20 are not particularly limited herein so long as they are anchor dependent cells.

As used herein "anchor dependent cells" are to be understood as cells that grow, survive or maintain function only when attached to a surface.

Examples of anchor dependent cells, or alternatively referred to as adhesive cells, are selected from the group consisting of: fibroblasts, myoblasts, myotube cells, corneal cells, vascular endothelial cells, smooth muscle cells, cardiomyocytes, dermal cells, epidermal cells, mucosal epithelial cells, mesenchymal stem cells, ES cells, iPS cells, osteoblasts, osteocytes, chondrocytes, fat cells, neurons, hair root cells, dental pulp stem cells, β-cells, hepatocytes, and combinations thereof. In the description herein the term "cells" refers not only to individual cells, but also includes cells constituting tissues collected from the body.

When the use of these cells in regenerative medicine in humans and the like is taken into consideration, preferably, autologous cells will be used. Cells of heterozoic origin can be used as long as they provide acceptable immunocompatibility, and among allogeneic cells, either heterologous or autologous cells can be used.

In one or more embodiments of the present invention, human mesenchymal stem cells (hMSCs) (Lonza, Walkersville, Md.) are used. Tissue engineering constructs based on cell sheets of the present invention allow increased cell-cell interactions and eliminate the risk of immunogenic materials present in scaffolds.

After creation of the cell culture support 10 cells are deposited onto the cured polymeric blend layer 14 and permitted to grow. In one or more embodiments, growth may occur, as is known in the art, in an incubator and/or in a nutrient bath. The cells are cultured by incubating in a warm (i.e. above LCST) medium according to normal specifications and then seeded onto the polymeric blend layer 14. After seeding, the cells are grown inside the incubator at 37° C. (≥LCST) to confluence to form the cultured cell sheet 16 and provide the cell culture complex 20.

The conditions (temperature, time) for culturing depends upon the specific cells to be cultured, but typically may range from about 33° C. to about 38° C. for a time of about 6 hours to about 30 days. The present invention advantageously uses simple technology and is devoid of techniques utilizing brushes or proteins.

Subsequently upon cells growing to confluence and forming the cell sheet 16, lowering the temperature of the cell culture complex 20, and particularly the temperature of the thermoresponsive polymer of the polymeric blend layer, to a temperature that is less than the LCST of the thermoresponsive polymer, causes the chains of the thermoresponsive polymer to expand, reducing the interaction between the cell sheet 16 and the entrapped TRP/coupling agent layer. Additionally, the entrapped TRP layer, as compared to pNIPAAm brushes, can uptake water more rapidly and result in a greater hydration/swelling of the layer, thus allowing for quick and easy detachment of the cell sheet 16.

Figure 2A:
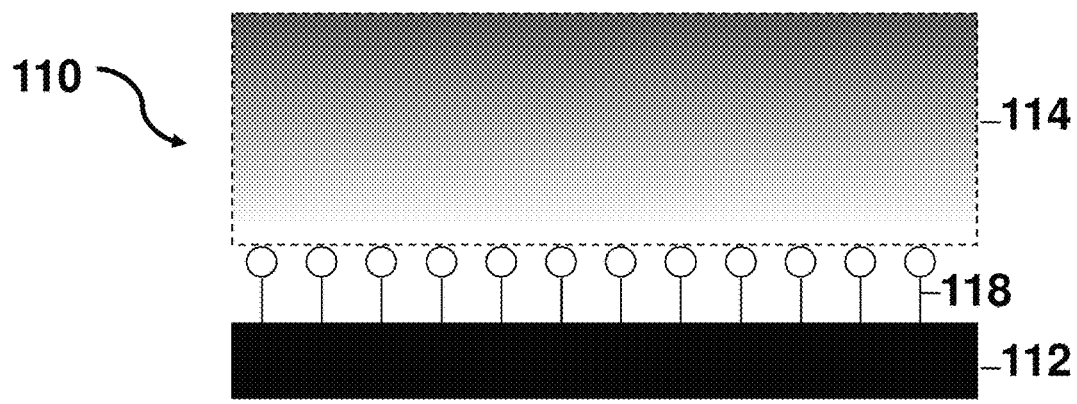
FIG. 2a schematically represents the application of a polymer blend of TESBA molecules/pNIPAAm chains to a substrate.
Figure 2B:
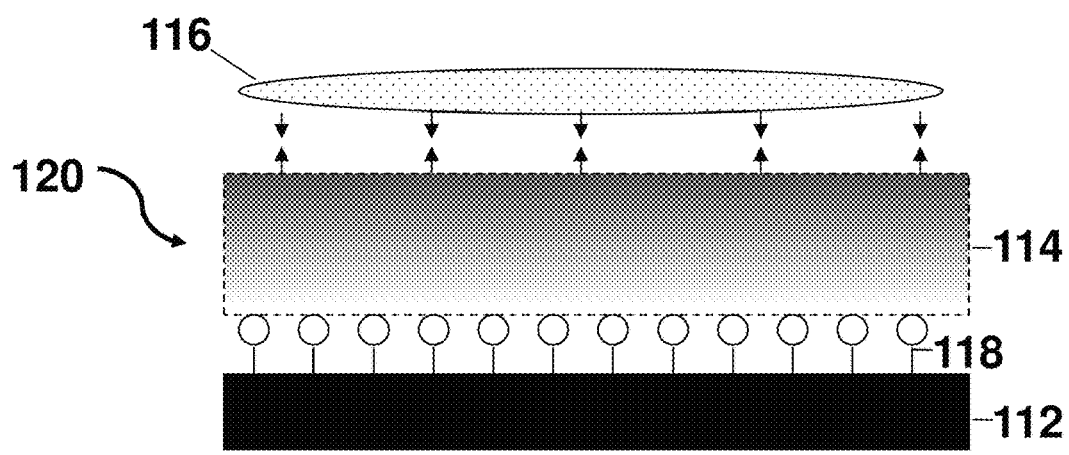
FIG. 2b schematically represents cell attachment and growth at a temperature above the LCST of pNIPAAm, when cells are attracted to the hydrophobic collapsed pNIPAAm layer.
Figure 2C:
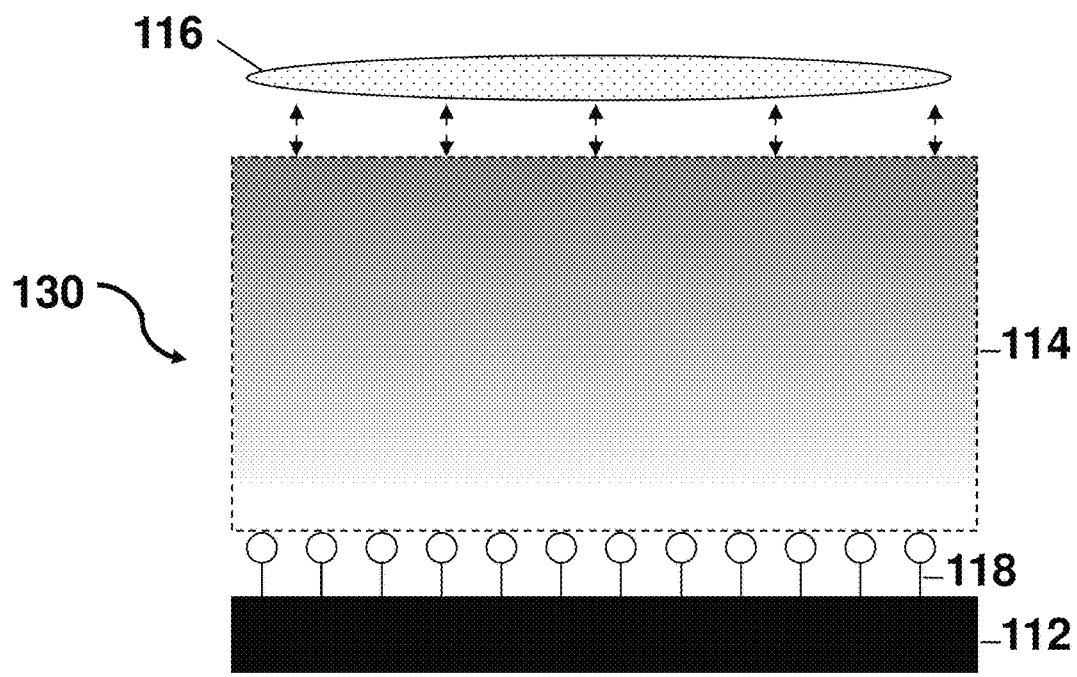
FIG. 2c schematically represents the hydrated pNIPAAm layer in the TESBA network as temperature is lowered to below LCST; the expanded chains become hydrophilic, which is unfavorable for cell adhesion, and cells detach from the pNIPAAm layer.

Without intending to be bound to a specific theory, a particular embodiment is schematically depicted in FIGS. 2a, 2b, and 2c, with reference to a cell culture support 110 having a glass substrate 112 and a polymeric blend layer 114 of pNIPAAm (TRP) and TESBA (coupling agent). In FIG. 2a, the polymer blend 114 is applied to the substrate 112 which further includes substrate functional groups 118, which may be —OH groups.

In FIG. 2b, cells 116 are applied and attached to the polymer blend layer with collapsed pNIPAAm chains (120). After cell attachment and growth (to confluent), a lowering in temperature to T<LCST leads to pNIPAAm chain extension and swelling of the blend layer (130), thus allowing cell sheet 116 detachment as shown in FIG. 2c.

Lowering the temperature of the cell culture medium, or replacing it with fresh room temperature medium, hydrates the pNIPAAm chains and changes their conformation to the extended form and the layer to be hydrophilic. Manipulating the amount of TESBA blended in pNIPAAm/TESBA films would control the amount of pNIPAAm retained or the extent of the layer swelling, thus the cell sheet detachment rate, which could play a significant role in future tissue engineering applications.

The thermoresponsive polymer/coupling agent blend, or more simply referred to as the polymer blend, of the present invention may be tailored to provide optimum cell attachment and, subsequently, rapid detachment for harvesting. Without being bound by theory, cell detachment is likely due to the extension of pNIPAAm chains and the hydration/swelling extent of the retained pNIPAAm layer. Increasing the amount of TESBA in the pNIPAAm/TESBA blend leads to, relatively, a smaller amount of pNIPAAm being retained, hence less hydration of the layer, leading to slower cell detachment upon cooling. For practical use, detachment times of less than 10 minutes are desired.

Referring again to FIG. 1a, the cell culture support 10 is comprised of a substrate 12 and a polymeric blend layer 14. Care in preparation of the substrates is taken to prevent contamination, which is important to the successful culturing of cells. The substrate 12 is first prepared to remove organic contaminants. This may be accomplished by immersing the substrates, such as non-limiting examples glass slides or silicon wafers, in a solution comprising 70 vol % $H_2SO_4$ and 30 vol % of 30% $H_2O_2$ or other suitable solution as is known in the art. The substrates are then rinsed with deionized water and dried with nitrogen gas followed by further cleaning in an UV/Ozone Cleaner for ten minutes.

In one or more embodiments of the present invention, a polymeric blend layer 14 may be prepared as follows. Separately, a 3 mass % pNIPAAm solution in ethanol and a 3 mass % TESBA solution in ethanol are prepared. The solutions are then blended in varying solution ratios of pNIPAAm:TESBA. In one or more embodiments, the blended solution may comprise about 3 mass % total solute. Solutions are filtered, for example using a PTFE membrane, to remove particulates. Polymer blend films are produced by spin-coating, or other thin film technique as previously described and as are known in the art, onto the prepared substrates. In one or more embodiments of the invention, a thin film of thermoresponsive polymer/coupling agent blend is spin-coated onto substrates for about 30 seconds at 2000 rpm to form a polymeric blend layer 14. The thickness of the polymeric blend layer typically ranges from about 200 nm to about 400 nm. The cell culture support 10 is then cured or annealed as previously described. In one or more embodiments, the cell culture supports are cured inside a vacuum for about one to three days at a temperature ranging from about 145° C. to about 205° C. to enable thermal annealing of the polymer blend network. After curing, the cell culture supports according to the present invention may be advantageously stored and/or transported for later use.

As shown in FIG. 1b, the cell culture complex 20 is comprised of a substrate 12, a cured polymeric blend layer 14, and a cultured cell layer 16. In one or more embodiments of the invention, cells are deposited onto the cured cell culture supports. In one or more embodiments, the cultured cell layer 16 includes culture medium specific to the particular cells chosen for culturing according to application and use. After depositing onto the cell culture support, the cells are grown to confluence to form a cultured cell layer 16, which may also be referred to as a cell sheet, to provide a cell culture complex 20.

According to at least one embodiment of the present invention after cells are grown to confluence to form a cultured cell layer 16, the cell sheet may be rapidly detached from the cell culture complex 20 for use in a variety of applications. The cell culture complex of the present invention advantageously achieves detachment without using mechanical agitations or proteolytic enzymatic means to aid detachment. In one or more embodiments, detachment of the cultured cell layer 16 is induced by replacing the warm cell culture medium with fresh room temperature medium. The cool medium acts to lower the temperature of the cell culture complex 20 below the LCST to provide for detachment of the cultured cell layer 16 within minutes. Alternatively in the absence of medium, other means of lowering the temperature of the cell culture complex below the LCST include refrigeration, soaking in cool water, or taking from warm place to room temperature, as well as other techniques as are known in the art.

In one or more embodiments of the present invention, the cell culture supports of the present invention may be used repeatedly. By using the supports more than once (typically supports may be used two to three times), the economic advantage of the present invention is yet furthered realized.

In order to demonstrate the practice of the present invention, the following examples have been prepared and tested. The examples should not, however, be viewed as limiting the scope of the invention. The claims will serve to define the invention.

Example 1

Materials.

pNIPAAm, a molecular weight of 20-40 kg/mol was purchased from Sigma Aldrich (St. Louis, Mo., USA). 3-Mercaptopropyl)trimethoxysilane (MPTMS), Triethoxysilylbutyraldehyde (TESBA), 3-Acetoxypropyltrimethoxysilane (AOPTMS) and 3-(2,3-Epoxypropoxy)propyltrimethoxysilane (EPPTMS) were from Gelest. Glass slides and P(100) test type silicon-wafers were purchased from Fisher Scientific (Waltham, Mass., USA) and Silicon Quest International (Santa Clara, Calif.), respectively. Polydimethylsiloxane (PDMS) sheet was prepared using Sylgard® 184 elastomer and its curing agent (Dow Corning, Midland, Mich.) according to the manufacture's recipe. Lexan™ polycarbonate (PC) sheets, ¼" thick, were purchased from Total Plastics Int'l (Middleburg Heights, Ohio). All other chemical reagents were purchased from Sigma Aldrich unless otherwise indicated.

Preparation of Glass, Silicon Wafer (Si-Wafer), Polydimethylsiloxane (PDMS) and Polycarbonate (PC) Substrates.

Glass slides and Si-wafers were cut into squares with a surface area of 1 cm$^2$. Slides and wafers were immersed in freshly prepared piranha solution (70 vol. % of concentrated H$_2$SO$_4$ and 30 vol. % of 30% H$_2$O$_2$) for 1 hour at 100° C. to remove organic contaminants. After decanting the piranha solution, the slides were thoroughly rinsed with deionized (DI) water and dried with nitrogen (N$_2$) gas. Afterwards, the slides and/or wafers were oxidized in a UV/Ozone Cleaner (Jelight Company Inc, Irvine, Calif.) for 10 minutes for further cleaning. PDMS or PC sheets were cut into squares with a surface area of ~1 cm$^2$, which were rinsed with ethanol and then oxidized in a plasma chamber (Harrick Plasma PDC-32G, Ithaca, N.Y.), using oxygen plasma at high power for 5 minutes.

Preparation of pNIPAAm/Coupling Agent Solutions.

A 1-3 mass % pNIPAAm solution and a 1-3 mass % coupling agent solution in ethanol (Pharmco-AAPER, Inc., Shelbyville, Ky.) were prepared separately. Solutions having pNIPAAm to coupling agent ratios (by mass) of 90:10, 80:20, 70:30, 60:40, 50:50, 40:60, 20:80 and 10:90 were prepared by mixing the proper ratios of the two above solutions and a small amount of ethanol to make a final solution containing 1-3 mass % of total solute. When using EPPTMS as the coupling agent, a separate approach can also be applied. In this approach, EPPTMS is added directly to pNIPAAm (in its solid form) to one of the ratios specified above and then diluted with ethanol to a final 1-3 mass %. The addition of EPPTMS to pNIPAAm first before diluting with ethanol allows the epoxy rings present in EPPTMS to covalently bind to the amine groups present in pNIPAAm, resulting in thicker films compared to predilution of EPPTMS and pNIPAAm then mixing them to obtain the needed ratio. The solutions were subsequently filtered to remove particulates through an Acrodisc® CR 13 mm Syringe filter with a 0.45 µm PTFE membrane (Pall Life Sciences, Co., Ann Arbor, Mich.).

Preparation of pNIPAAm/Coupling Agent Films.

Polymer blend films were produced by spin coating the pNIPAAm/coupling agent mixed solution onto pre-cleaned substrates for 30 seconds at 2000 rpm (p-6000 Spin Coater, Specialty Coating Systems, Inc, Indianapolis, Ind.). The spin-coated samples were cured inside a vacuum (<100 mTorr) oven (VWR International, Radnor, Pa.) for 1-3 days at the following temperatures 160° C.

Water Contact Angles on pNIPAAm/Coupling Agent Thin Films.

The sessile drop method was utilized to measure the advancing and static water contact angles on the pNIPAAm/coupling agent films. Advancing and static contact angles were measured at 40° C. and 25° C. by placing the sample on the heating stage (TP-110R, TOKAI HIT) and observing the water droplet using a goniometer (Ramé-Hart Instrument Co, Netcong, N.J.). After the heating stage reached the set temperature (40° C. or 25° C.), the sample was placed on the stage and allowed to equilibrate for ~5 min. Then, a water drop (~10 µl) was placed on the sample, with the needle in the drop, and more water was slowly added until the drop was ready to advance, at which point the image was captured. The time from adding the drop to taking the image was ~1 min. After two advancing measurements, the needle was withdrawn, and the drop (~20 µl) was allowed to sit on the sample for ~1 min before the image was taken for the static contact angle. The contact angles were measured from the captured images using ImageJ software (National Institutes of Health, Bethesda, Md.).

Thickness of pNIPAAm/Coupling Agent Films.

A manual photoelectric ellipsometer (Rudolph Instruments, Inc., Fairfield, N.J.) was used to measure the thicknesses of different pNIPAAm/coupling agent films on Si-wafers at a 632 nm wavelength. A refractive index of 1.47 for pNIPAAm was used for thickness calculations for the blended films, which might have a slightly different refractive index compared to a pure pNIPAAm film. Thickness measurements were taken of films made with different pNIPAAm/coupling agent ratios and/or cured at different temperatures. Samples were measured before and after immersion in cold DI water (immersed samples were dried by a stream of nitrogen before measurement). Two thickness measurements for each sample, and multiple samples (n=3) treated under the same condition were measured to provide the statistical values.

Cell Attachment.

Normal Human Dermal Fibroblast cells (NHDF) (Lonza, Walkersville, Md.) were cultured in FBM fibroblast medium (Lonza) supplemented with FGM-2 SingleQuots Kit (Lonza) according to manufacturer's specifications. Also mouse embryonic fibroblast cells (NIH3T3, ATCC, Manassas, Va.) were cultured in Dulbecco's Modified Engle Medium (DMEM, Sigma-Aldrich, St. Louis, Mo.) supplemented with 10% fetal bovine serum (FBS, Sigma-Aldrich) and 1% of antibiotic antimycotic solution (100×, Sigma-Aldrich). To observe cell attachment, NHDF or NIH3T3 (Passage 4, 5, 6, 7 or 8) were seeded onto different substrates: a clean glass substrate, a clean PC sheet, a 90:10 or a 50:50 pNIPAAm/coupling agent film cured at 160° C. on glass or PC, at a density of 1.5×10$^4$ cells/cm$^2$. Phase contrast microscopic images were taken 1 day, 2 days, or 3 days after cell seeding on each of the surfaces using an Olympus IX71 (B & B Microscopes, Ltd., Pittsburgh, Pa.) microscope equipped with an eyepiece camera.

Cell Sheet Detachment.

After the cells grew to confluence and formed a cell sheet on the pNIPAAm/coupling agent film, detachment was induced by placing the sample outside the incubator and replacing the cell culture medium with a fresh room temperature (23° C.) medium. Cells grown on UpCell® dishes were used for comparisons. Time lapse images were taken using software that communicates with the eyepiece camera to monitor cell detachment behavior. A sequence of images was captured with a preset time interval (5 s, 10 s, 20 s or 30 s) until the entire sheet or attached cells were detached.

pNIPAAm/Coupling Agent Blend Films Support Cell Attachment and Proliferation.

NHDF or NIH3T3 cells were seeded on different substrates and observed under a phase contrast microscope. After 1 day, 2 days or 3 days of seeding, cell attachment and spreading was observed on all the surfaces, and a full cell sheet was found after 3 days of incubation. For cells on glass, cell sheet detachment was observed on the pNIPAAm/coupling agent films, but not on the uncoated glass slide.

General Properties of pNIPAAm/Coupling Agent Films.

Prepared solutions were all transparent, indicating complete dissolution of the pNIPAAm/coupling agent mixture in ethanol. Films spin-coated on silicon wafers appeared to have a uniform color throughout the sample except at the edges where a slightly thicker film might result. There was a slight color change of each sample before and after curing, indicating a slight change in film thickness by thermal curing. Films cured at <150° C. appeared to completely dissolve away when dipped into or rinsed by DI water at room temperature (~25° C.<LCST). Films cured at higher temperatures (160° C. to 205° C.) underwent a color change, but were still retained on the substrate. The ellipsometry measurements, referring to Table 1a & b, showed that after rinsing by DI water at room temperature, normally 10-90% of the film was removed or (i.e., 90-10% of the film was retained) from a pNIPAAm/coupling agent film cured at 160° C. and above. The % of film retained depended on the ratio of the pNIPAAm/coupling agent, the mass % of solute and the type of coupling agent used. Thickness of films after rinsing by room temperature cell culture medium was also measured and was found to be not significantly different from that of films after rinsing by DI water. A prolonged (e.g. 3 days) immersion in room temperature water showed some additional reduction in thickness (≤10%).

TABLE 1a

Thickness of Films prepared on Si-wafer using two different pNIPAAm/coupling agent ratios (2 mass %) and cured at 160° C. for 3 days before and after rinsing by room temperature DI water.

| | Thickness (nm) | | | |
|---|---|---|---|---|
| | 90/10 pNIPAAm/ coupling agent | | 50/50 pNIPAAm/ coupling agent | |
| coupling agent | initial film | after rinsing | initial film | after rinsing |
| TESBA | 95.4 ± 4.8 | 30.0 ± 9.0 | 53.2 ± 5.4 | 31.0 ± 8.1 |
| MPTMS | 95.6 ± 6.7 | 9.4 ± 1.9 | 47.5 ± 9.5 | 8.6 ± 2.6 |
| AOPTMS | 92.1 ± 1.0 | 25.9 ± 5.2 | 49.2 ± 5.0 | 12.8 ± 2.6 |
| EPPTMS | 88.1 ± 4.5 | 67.6 ± 4.1 | 49.8 ± 8.0 | 44.0 ± 5.3 |

TABLE 1b

Film thickness of some prepared (spin-coated from 1 mass % of total solute, cured at 160° C. for 3 days) pNIPAAm/coupling agent films on polycarbonate (PC) before and after rinsing by room temperature DI water.

| pNIPAAm/coupling agent, ratio | Thickness (nm) | |
|---|---|---|
| | initial film | after rinsing |
| pNIPAAm/TESBA, 90/10 | 22.1 ± 1.2 | 15.3 ± 0.8 |
| pNIPAAm/TESBA, 50/50 | 16.2 ± 0.9 | 7.8 ± 0.4 |
| pNIPAAm/TESBA, 10/90 | 2.9 ± 0.2 | 2.6 ± 0.1 |
| pNIPAAm/MPTMS, 50/50 | 13.3 ± 0.7 | 10.2 ± 0.5 |
| pNIPAAm/EPPTMS, 50/50 | 14.0 ± 0.8 | 10.4 ± 0.6 |

Water contact angles confirmed pNIPAAm/coupling agent films were thermo-responsive. The static water contact angle decreased with a decrease in temperature, dropping from an angle of ~60° at a temperature of 40° C. (above the LCST of pNIPAAm) to about 40-50° at a temperature of ~25° C. (below the LCST of pNIPAAm, Table 2a). The advancing water contact angle also showed a decrease with a decrease in temperature, dropping from an angle of 80-90° at a temperature of 40° C. to about 70° at a temperature of ~25° C. (Table 2b). In general, the contact angle change rapidly occurred in the temperature range of 31-34° C. for the pNIPAAm/coupling agent films cured at 160° C. or above for 3 days.

TABLE 2a

Advancing water contact angles of some prepared pNIPAAm/coupling agent films on Si-wafer (cured at 160° C. for 3 days) after the films were thoroughly rinsed by room temperature DI water.

| coupling agent | Static water contact angles, θs (°) | |
|---|---|---|
| | at 40° C. | at 25° C. |
| TESBA | 58.8 ± 0.6 | 45.8 ± 0.5 |
| MPTMS | 58.7 ± 1.2 | 46.8 ± 1.5 |
| AOPTMS | 58.0 ± 0.6 | 52.0 ± 0.6 |
| EPPTMS | 63.1 ± 1.9 | 39.5 ± 0.8 |

TABLE 2b

Advancing water contact angles of some pNIPAAm/coupling agent films on polycarbonate (PC), spin-coated from 1 mass % of total solute and cured at 160° C. for 3 days, before and after rinsing by room temperature DI water.

| pNIPAAm/coupling agent, ratio | Advancing water contact angle, $\theta_A$ (°) | |
|---|---|---|
| | at 40° C. | at 25° C. |
| pNIPAAm/TESBA, 90/10 | 88.4 ± 1.1 | 74.9 ± 4.7 |
| pNIPAAm/TESBA, 50/50 | 84.9 ± 2.9 | 69.2 ± 4.2 |
| pNIPAAm/TESBA, 10/90 | 79.5 ± 2.9 | 75.6 ± 3.2 |
| pNIPAAm/MPTMS, 50/50 | 82.6 ± 3.3 | 66.4 ± 2.6 |
| pNIPAAm/EPPTMS, 50/50 | 84.1 ± 2.4 | 66.6 ± 2.3 |

By simply blending a solution of EPPTMS in ethanol with a solution of pNIPAAm in ethanol, the retained film was thinner as compared to the film prepared by blending EPPTMS with pNIPAAm first, and then the mixture was dissolved in ethanol. Some of the example coatings are summarized in Table 3 below.

TABLE 3

Film thickness and retention of pNIPAAM/EPPTMS films prepared differently and cured at 160° C. for 3 days and the corresponding advancing water contact angles on their rinsed films.

| ratio (total mass % solute) (method) | Initial film thickness (nm) | % film retained after rinsing | Advancing water contact angle, $\theta_A$ (°) | |
|---|---|---|---|---|
| | | | at 40° C. | at 25° C. |
| 50/50 (1 mass %) (blend the solutions) | 14.0 ± 0.8 | 74 | 84.1 ± 2.4 | 66.6 ± 2.3 |
| 50/50 (1 mass %) (EPPTMS + pNIPAAm, then add ethanol) | 12.2 ± 0.7 | 98 | 83.9 ± 3.6 | 76.1 ± 3.2 |
| 10/90 (1 mass %) (EPPTMS + pNIPAAm, then add ethanol) | 24.0 ± 1.3 | 83 | 83.2 ± 5.1 | 66.4 ± 2.0 |

Cell Detachment on pNIPAAm/Coupling Agent Films.

NIH3T3 cells were cultured on pNIPAAm/coupling agent films to assess individual cell and cell sheet detachment resulting from temperature change. Upon 80% confluence, cell detachment was achieved by replacing the cell culture medium with fresh room temperature (~25° C.) medium. All cells detached within 5 minutes after adding cool medium. Under the same conditions, it took nearly 3 hours for the cells to completely detach from the commercial thermo-responsive cell culture surface (UpCell®).

Figure 3:
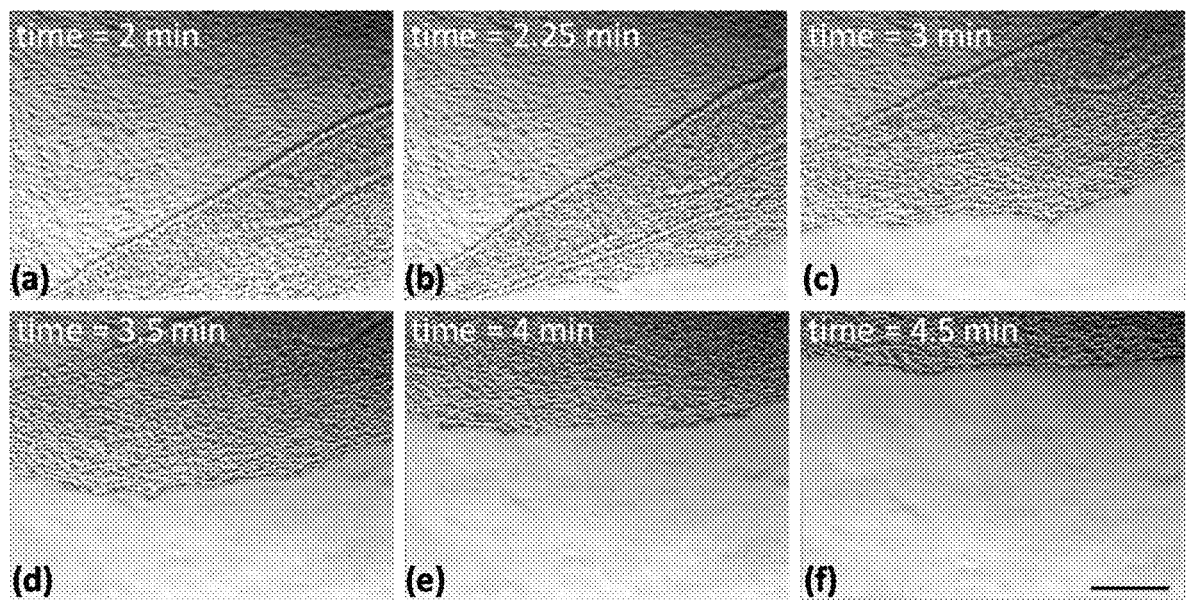
FIG. 3 shows multiple images of the detachment of a NIH3T3 cell sheet from a 50/50 pNIPAAm/MPTMS film coated on a glass slide after 2 minutes (a); after 2.25 minutes (b); after 3 minutes (c); after 3.5 minutes (d); after 4 minutes (e); and after 4.5 minutes (f).

The cell sheet detachment was assessed the same way as the aforementioned individual cell detachment. After adding cool medium, the confluent cell sheet detached from one end and rolled up or slid (as shown in the various images of FIG. 3). The entire detachment process took approximately 5 minutes from the point cool medium was added to when all cells had detached from the 90:10 or 50:50 160° C. cured pNIPAAm/TESBA or MPTMS film. Cell viability before and after detachment was also examined using trypan blue staining. Minimal cell death after detachment from our surface, revealing that the detachment process does not harm the cells significantly. UpCell® surfaces were found to take much longer (>3 hours) for the cell sheet to completely detach when using the same protocols.

Cellular Behavior on pNIPAAm Films.

pNIPAAm films produced according to the present invention provide surfaces that are biocompatible and support the maintenance of normal cellular functions. Furthermore, cell culture supports of the present invention provide cell attachment regardless of film thickness.

Cell culture supports of the present invention further provide rapid cell detachment with room temperature medium. The detachment could be the combination of passive detachment due to the hydration of the pNIPAAm chains that make the surface less favorable for the cells and active detachment by cells signaling to each other to reorganize their cytoskeleton under the unfavorable environment.

What is claimed is:

1. A method of making a cell culture complex comprising:
   providing a substrate;
   blending at least one thermoresponsive polymer and at least one coupling agent having functional thiol, ester, epoxy, or aldehyde groups to provide a polymeric blend;
   applying a thin film of said polymeric blend to the substrate to provide a polymeric blend layer on the substrate;
   curing the polymeric blend layer on the substrate to provide a cell culture support such that the at least one coupling agent forms a three-dimensional multilayered network which entraps the at least one thermoresponsive polymer; and
   depositing cells onto said cell culture support to form a cultured cell layer, wherein the cells may optionally further comprise medium, to provide a cell culture complex.

2. The method of claim 1, wherein the cultured cell layer comprises cells further characterized as anchor dependent cells.

3. The method of claim 1, wherein the cultured cell layer comprises cells further characterized as adhesive cells.

4. The method of claim 1, wherein the cultured cell layer comprises cells selected from the group consisting of fibroblasts, myoblasts, myotube cells, corneal cells, vascular endothelial cells, smooth muscle cells, cardiomyocytes, dermal cells, epidermal cells, mucosal epithelial cells, mesenchymal stem cells, ES cells, iPS cells, osteoblasts, osteocytes, chondrocytes, fat cells, neurons, hair root cells, dental pulp stem cells, β-cells, hepatocytes, and combinations thereof.

5. The method of claim 1, wherein the cultured cell layer comprises cells and medium.

6. The method of claim 1, wherein the thin film of said polymeric blend is spin-coated onto the substrate.

7. The method of claim 1, wherein the polymeric blend layer is devoid of adhesive proteins, plasma treatment, and e-beam treatment; and wherein the method of claim 1 further includes a step of detaching the cultured cell layer, and wherein the step of detaching is devoid of the use of proteolytic enzymes or mechanical agitations.

8. The method of claim 1, wherein the step of blending further includes creating a first solution of the at least one coupling agent in ethanol, creating a second solution of the at least one thermoresponsive polymer in ethanol, and combining the first solution with the second solution to provide the polymeric blend.

9. The method of claim 1, wherein the step of blending further includes creating a mixture of the at least one coupling agent and the at least one thermoresponsive polymer and dissolving the mixture in ethanol to provide the polymeric blend.

10. The method of claim 1, wherein the at least one thermoresponsive polymer is selected from the group consisting of poly (N-isopropylacrylamide)(PNIPAAm), poly (N,N-diethylacrylamide) (PDEAAm), poly(N-vinlycaprolactam) (PVCL), poly[2-(dimethylamino)ethyl methacrylate] (PDMAEMA), poly(ethylene oxide) (PEO), 2-oxazoline (Pox), poly(2-ethyl-2-oxazoline), poly(2-cyclopropyl-2-oxazoline), poly(2-n-propyl-2-oxazoline), poly(2-isopropyl-2-oxazoline); poly(2-ethyl-oxazine), poly(2-n-propyl-oxazine), and combinations thereof.

* * * * *